(12) United States Patent
Shirasuka

(10) Patent No.: US 8,215,953 B2
(45) Date of Patent: Jul. 10, 2012

(54) ORTHODONTIC BRACKET

(76) Inventor: Naoki Shirasuka, Tokyo (JP)

( * ) Notice: Subject to any disclaimer, the term of this patent is extended or adjusted under 35 U.S.C. 154(b) by 751 days.

(21) Appl. No.: 11/582,111

(22) Filed: Oct. 16, 2006

(65) Prior Publication Data

US 2007/0048686 A1 Mar. 1, 2007

Related U.S. Application Data

(63) Continuation-in-part of application No. 10/897,587, filed on Jul. 23, 2004, now abandoned.

(30) Foreign Application Priority Data

| Dec. 5, 2003 | (JP) | ................... | 2003-406992 |
| Dec. 11, 2003 | (JP) | ................... | 2003-412703 |
| Jun. 24, 2004 | (JP) | ................... | 2004-185770 |

(51) Int. Cl.
*A61C 3/00* (2006.01)

(52) U.S. Cl. .......................................................... 433/9

(58) Field of Classification Search .............. 433/8–16, 433/24

See application file for complete search history.

(56) References Cited

U.S. PATENT DOCUMENTS

| 4,819,316 A * | 4/1989 | Rossini et al. .................... 433/8 |
| 5,238,402 A | 8/1993 | Rohlcke et al. |
| 5,304,061 A | 4/1994 | Nelson |
| 5,464,347 A * | 11/1995 | Allesee .............................. 433/8 |
| 5,595,484 A | 1/1997 | Orikasa et al. |
| 5,607,299 A | 3/1997 | Nicholson |
| 5,692,898 A | 12/1997 | Orikasa et al. |
| 5,711,665 A * | 1/1998 | Adam et al. ...................... 433/9 |
| 5,803,728 A | 9/1998 | Orikasa et al. |
| 5,993,206 A * | 11/1999 | Andreiko .......................... 433/9 |
| 6,280,185 B1 * | 8/2001 | Palmer et al. ..................... 433/8 |
| 6,305,932 B1 * | 10/2001 | Mottate ............................. 433/8 |
| 2003/0170584 A1 | 9/2003 | Andreiko |

OTHER PUBLICATIONS

Paint. (n.d.). Dictionary.com Unabridged (v 1.1). Retrieved Sep. 4, 2007, from Dictionary.com website: http://dictionary.reference.com/browse/paint.*

* cited by examiner

*Primary Examiner* — Heidi M Eide
(74) *Attorney, Agent, or Firm* — Stetina Brunda Garred & Brucker

(57) ABSTRACT

Orthodontic brackets that can accurately be mounted to the surface of teeth to effectively perform orthodontic treatment. The orthodontic bracket according to the present invention is characterized in that, a marker is provided on at least a portion of an outline that is generated by crossing a plane including a longitudinally extending center line, on the archwire slot base of the archwire slot and vertical to the archwire slot base, and an outer surface of the bracket with each other. The marker can be selected from the group consisting of a protrusion, a projection, a slit, a notch and a paint. Another orthodontic bracket according to the present invention has an insert hole drilled from an outer surface of the bracket to a portion just before a base of the body along a line passing through a point that is generated by crossing a line, which is generated by crossing a plane including a longitudinally extending center line, on the archwire slot base of the archwire slot and vertical to the archwire slot base, and the body base, and a plane vertical to the center line of the archwire slot and dividing the body exactly into two parts. This bracket is especially preferably used for indirect method as well as direct method.

20 Claims, 5 Drawing Sheets

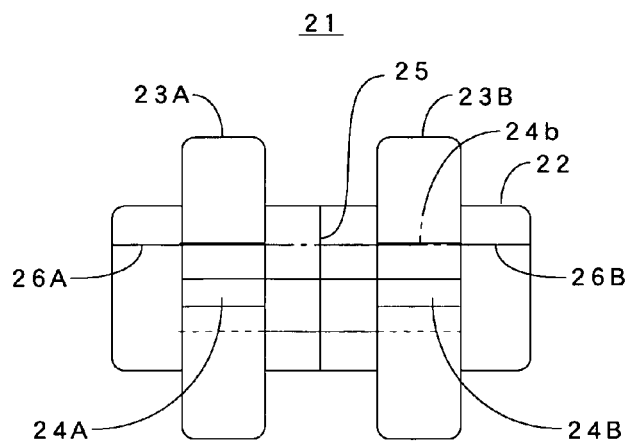
Fig. 1B
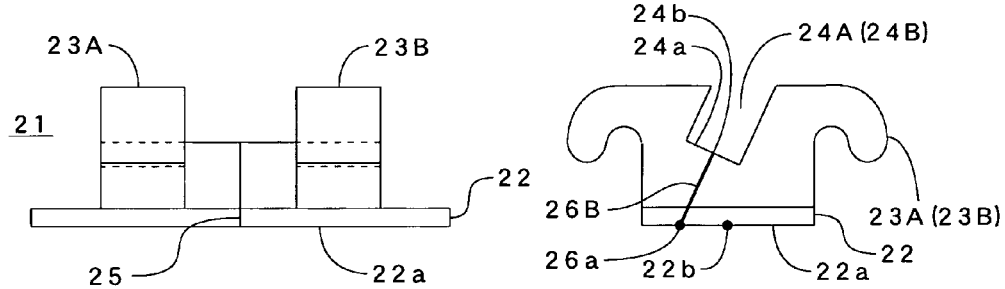
Fig. 1A
Fig. 1C
Fig. 2
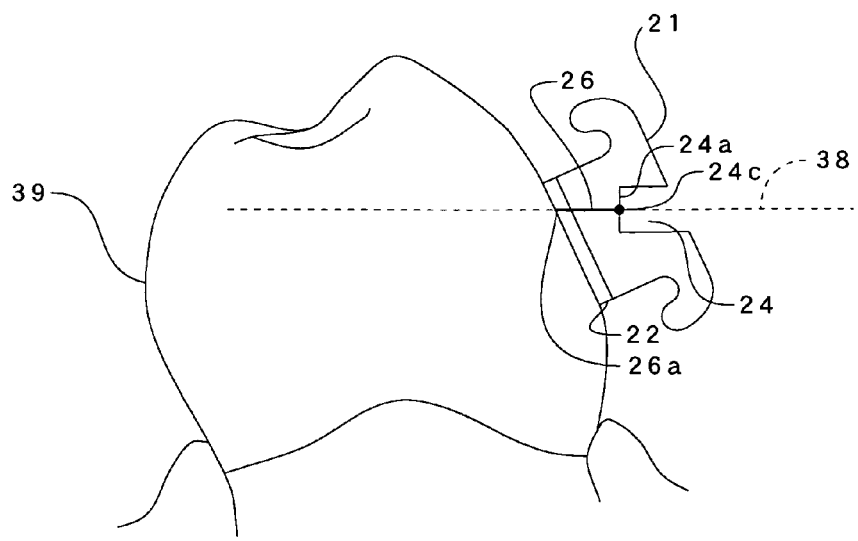

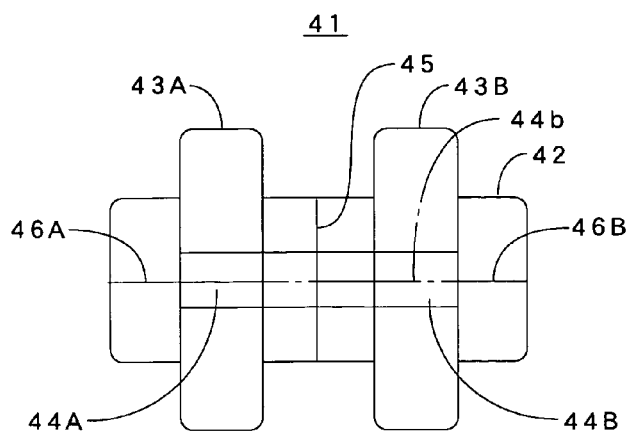
Fig. 3B
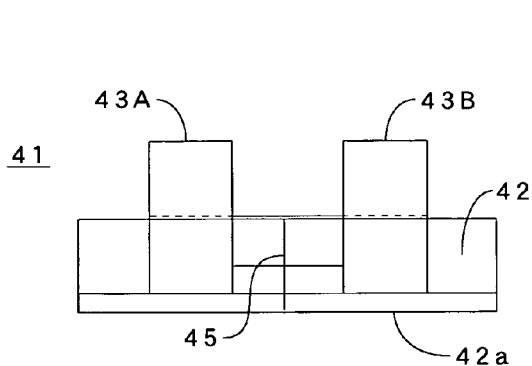
Fig. 3A
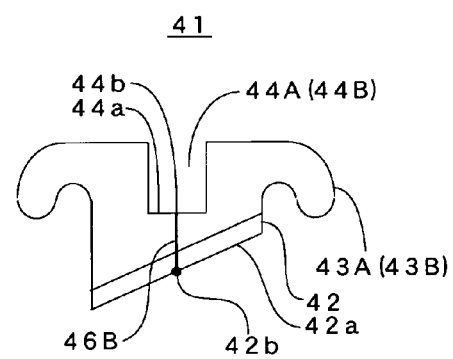
Fig. 3C
Fig. 4
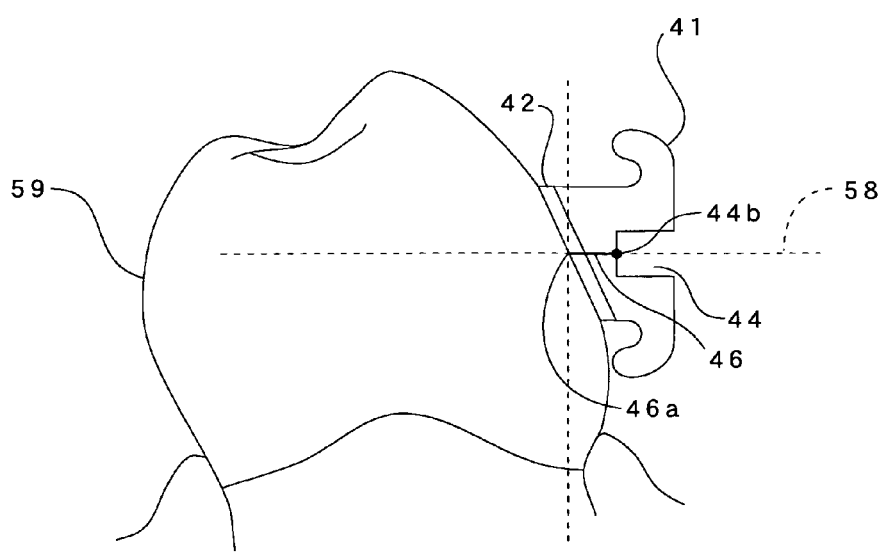

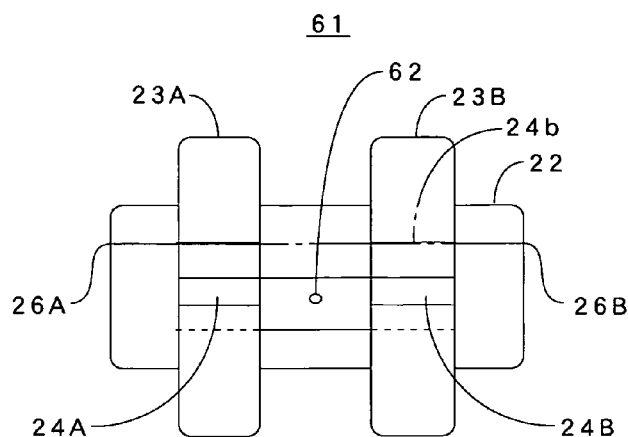
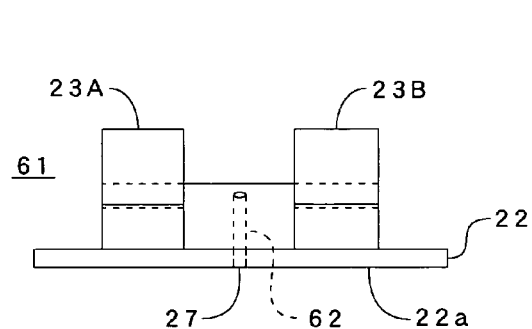 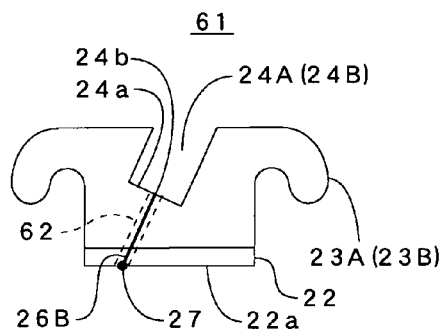
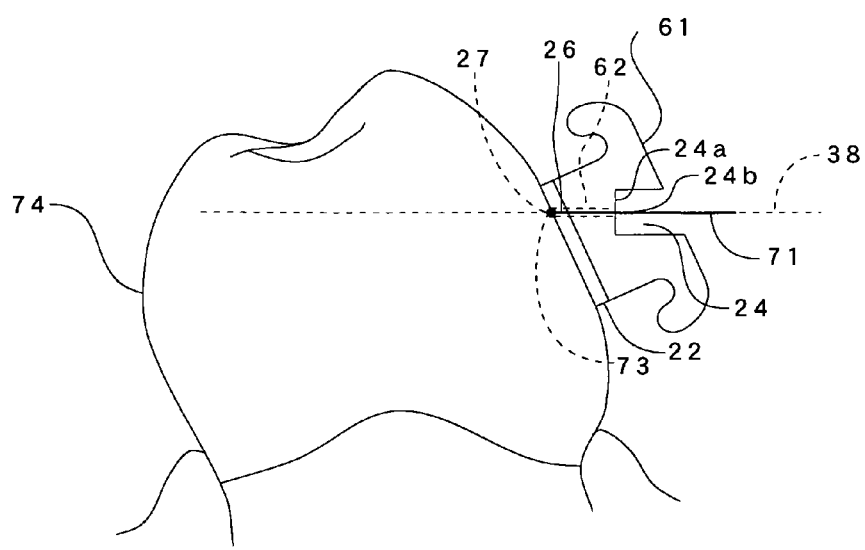

ORTHODONTIC BRACKET

CROSS-REFERENCE TO RELATED APPLICATIONS

The present application is a continuation-in-part of U.S. application Ser. No. 10/897,587 entitled ORTHODONTIC BRACKET filed Jul. 23, 2004 now abandoned which claims priority to Japanese Patent Application No. 2003-406992 filed Dec. 5, 2003, which claims priority to Japanese Patent Application No. 2003-412703 filed on Dec. 11, 2003 and which claims priority to Japanese Patent Application No. 2004-185770 filed on Jun. 24, 2004.

STATEMENT RE: FEDERALLY SPONSORED RESEARCH/DEVELOPMENT

Not Applicable

BACKGROUND

1. Field of the Invention

The present invention relates to orthodontic brackets that are easily positioned at orthodontically correct locations on the patient's teeth to effectively perform orthodontic treatment.

2. Description of the Related Art

In orthodontic treatment, orthodontic brackets made of metal or the like are bonded to the patient's teeth through bonding agent; the orthodontic brackets are fastened by a thin archwire; and an external force is applied to the orthodontic brackets through the archwire to move the teeth subjected to treatment to correct locations.

When an orthodontic bracket is bonded to the patient's tooth, as shown in FIG. 7, a vertical center line 85 of a bracket 84 should be overlapped with a facial axis of a clinical crown (hereinafter referred to as "FACC") 81, and a base point 88 that is the point where a line passing the center 86b of the base 86a of the archwire slot 86 and vertical to the base 86a crosses the base 87 of the bracket 84 should be coincided with a mid-transverse plane 82. If the bracket 84 is not positioned properly as described above, load of an archwire cannot be applied properly to the tooth through the bracket 84, resulting in insufficient orthodontic treatment.

In order to overlap the vertical center line of the bracket to the FACC, a variety of brackets with markers have been used. Meanwhile, in order to coincide the base point of the bracket to the mid-transverse plane of the tooth, for example, a gage partially fixed to an archwire slot of the bracket is used to bond the bracket to the tooth with the distance between an incisal margin or a cusp of the tooth and the slot being measured by the gage. However, since the base point of the bracket and the surface of the tooth are apart from each other, and manners abutting the gage to the teeth should be changed in accordance with the position of the tooth in a row of the patient's teeth, it is not easy to coincide the base point of the bracket to the mid-transverse plane of the tooth with the gage.

On the other hand, Japanese Patent Publication (Unexamined) No. Heisei 8-112293 discloses an orthodontic bracket that can be bonded to a correct position, which is parallel to the FACC and the occlusal plane. This bracket is provided with a visible standard line, which is to be parallel to the FACC, on the center line of a pair of tiewings, and another visible standard line, which is to be parallel to the occlusal plane, on a slot line crossing the former standard line. Then, orthodontists can adjust the location of the bracket while positively utilizing the standard lines.

As described above, when a bracket is mounted to a tooth, it is necessary to coincide the vertical center line of the bracket to the FACC as well as the base point to the mid-transverse plane. But, it is not easy to do so with the above-mentioned gage. With the bracket shown in the above document, standard lines are provided on the center line of a pair of tiewings and on the slot line only, so that it is not easy to coincide the base point of the bracket and the mid-transverse plane of the tooth with each other.

Especially, as illustrated in FIG. 8, when a torque-in-face-type bracket is used, in order to coincide a base point 98 of a bracket 90 to a mid-transverse plane 92 of a tooth 96 to be treated, it is necessary to coincide the base point 98 to a facial-axis point (hereinafter referred to as "FA point") 94 where the FACC of the tooth 96 and the mid-transverse plane 92 cross with each other. However, since the FA point 94 and a line passing the center 99b of the base 99a of the body 99 and vertical to the base 99a are remarkably apart from each other, it is not easy to coincide the base point 98 of the bracket 90 to the FA point 94.

SUMMARY OF THE INVENTION

It is therefore the object of the present invention to provide brackets in which the base point of the bracket can easily be coincided to the mid-transverse plane, resulting in effective orthodontic treatment.

To accomplish the above objective, an orthodontic bracket according to the present invention with a body defining a body base and an archwire slot defining an archwire slot base, in which the body base and the archwire slot base being disposed in a non-parallel relationship with one another, is characterized in that, a marker is provided on at least a portion of an outline that is generated by crossing a plane including a longitudinally extending center line, on the archwire slot base of the archwire slot and vertical to the archwire slot base, and an outer surface of the bracket with each other.

With the above orthodontic bracket according to the present invention, coinciding the marker provided on at least a portion of the outline to the mid-transverse plane of a tooth, to which the bracket is bonded, allows the base point of the bracket to be positioned on the mid-transverse plane, further, coinciding the center of the bracket to the FACC causes the bracket to accurately be positioned on the tooth to be treated, resulting in effective orthodontic treatment.

In the afore-mentioned bracket according to the present invention, the marker may be selected from the group consisting of a protrusion, a projection, a slit, a notch and a paint.

Further, an orthodontic bracket according to the present invention with a body defining a body base and an archwire slot defining an archwire slot base, in which the body base and the archwire slot base being disposed in a non-parallel relationship with one another, is characterized in that, an insert hole is drilled from an outer surface of the bracket to a portion just before a base of the body along a line passing through a point that is generated by crossing a line, which is generated by crossing a plane including a longitudinally extending center line, on the archwire slot base of the archwire slot and vertical to the archwire slot base, and the body base, and a plane vertical to the center line of the archwire slot and dividing the body exactly into two parts.

With the above orthodontic bracket according to the present invention, inserting a needle-like jig into the insert hole causes the FA point of the tooth to be treated and the target point for positioning of the bracket to substantially be coincided with each other, which not only causes the bracket to be mounted in ease in direct method, but the bracket is effective to indirect method also, in which a bracket is preliminarily bonded on a model of the patient's row of teeth at a position where the bracket should be mounted, and then, the bracket is properly transported in the oral cavity of the patient and is bonded to the patient's tooth.

Still further, an orthodontic bracket according to the present invention with a body defining a body base and an archwire slot defining an archwire slot base, in which the body base and the archwire slot base being disposed in a non-parallel relationship with one another, is characterized in that, a through hole penetrates the body from the base of the body to an outer surface of the bracket along a line passing through a point that is generated by crossing a line, which is generated by crossing a plane including a longitudinally extending center line, on the archwire slot base of the archwire slot and vertical to the archwire slot base, and the body base, and a plane vertical to the center line of the archwire slot and dividing the body exactly into two parts.

With the above orthodontic bracket according to the present invention also, inserting a needle-like jig into the through hole causes the FA point of the tooth to be treated and the target point for positioning of the bracket to substantially be coincided with each other, which makes it easy to mount the bracket in direct method, and is effective to indirect method also.

The orthodontic bracket with the insert hole or the through hole described above may further comprises a marker provided on at least a portion of an outline that is generated by crossing the plane including the longitudinally extending center line, on the archwire slot base of the archwire slot and vertical to the archwire slot base, and an outer surface of the bracket with each other.

With this construction, substantially coinciding the FA point of the tooth to be treated and the target point for positioning of the bracket with each other, and further coinciding the marker to the mid-transverse plane of the tooth, to which the brackets is mounted, causes the bracket to remarkably accurately be positioned on the tooth to be treated with ease. And, the marker can be selected from the group consisting of a protrusion, a projection, a slit, a notch and a paint.

BRIEF DESCRIPTION OF THE DRAWINGS

The present invention will be more apparent from the ensuring description with reference to the drawings, wherein:

FIGS. 1A to 1C show an orthodontic bracket according to the first embodiment of the present invention, in which FIG. 1A is a front view, FIG. 1B a plan view and FIG. 1C a side view;

FIG. 2 is a drawing for explaining the usage of the bracket shown in FIGS. 1A to 1C;

FIGS. 3A to 3C show an orthodontic bracket according to the second embodiment of the present invention, in which FIG. 3A is a front view, FIG. 3B a plan view and FIG. 3C a side view;

FIG. 4 is a drawing for explaining the usage of the bracket shown in FIGS. 3A to 3C;

FIGS. 5A to 5C show an orthodontic bracket according to the third embodiment of the present invention, in which FIG. 5A is a front view, FIG. 5B a plan view and FIG. 5C a side view;

FIG. 6 is a drawing for explaining the usage of the bracket shown in FIGS. 5A to 5C;

FIGS. 7A to 7D are drawings for explaining a manner to mount a conventional bracket to a tooth, in which FIG. 7A is for explaining a standard line and a standard point of the tooth, FIG. 7B is a plan view for explaining the manner to mount the bracket to the tooth, FIG. 7C is a side view of the bracket and the tooth shown in FIG. 7B, and FIG. 7D is an enlarged view showing the bracket on the tooth.

DETAILED DESCRIPTION OF PREFERRED EMBODIMENTS

Now, preferred embodiments of the present invention will be explained with reference to drawings.

FIGS. 1A to 1C and FIG. 2 show an orthodontic bracket according to the first embodiment of the present invention. This bracket 21 is provided with tiewings 23 (23A, 23B) and archwire slots (hereinafter referred to as "slots") 24 (24A, 24B) on a body 22, and is a so-called torque-in-base type bracket. The body 22 includes a pad portion, which is the same in other embodiments described below.

Figures 7A, 7B, 7C:
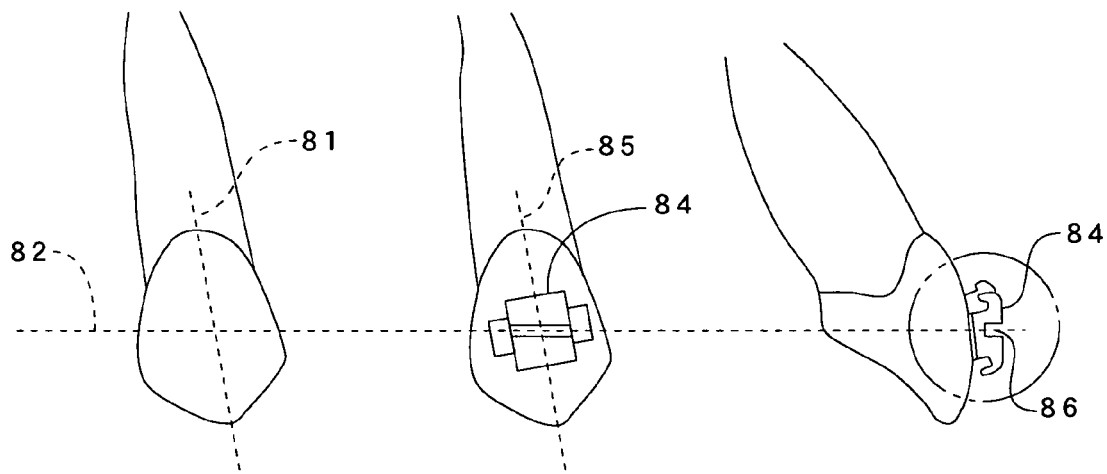
Figure 7D:
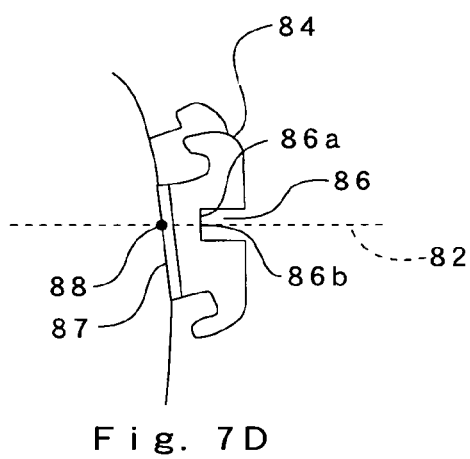
Figure 8:
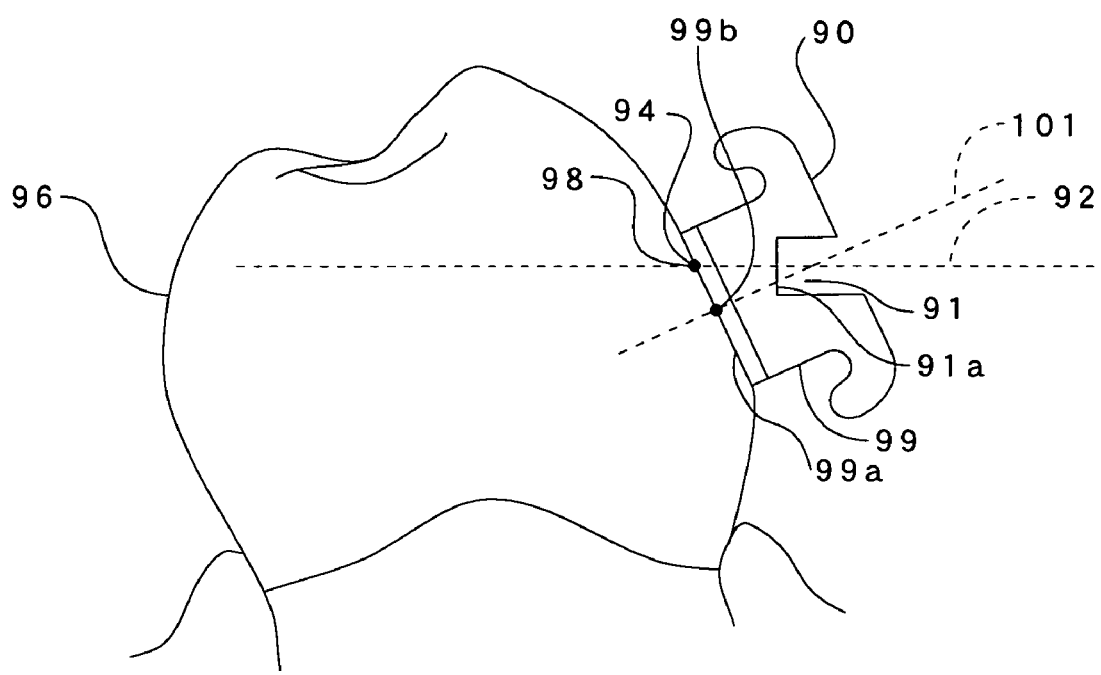
FIG. 8 is a schematic view for explaining a manner to mount a conventional torque-in-face-type bracket to a tooth.

The torque-in-face-type bracket is, as shown in FIGS. 1C and 2, characterized in that the bracket 21 is provided with bases 24a of slots 24 (24A, 24B) and a base 22a of a body 22 are not parallel with each other; and a plane including a longitudinally extending center line 24b, on the base 24a of the archwire slot 24, of the archwire slot 24 and vertical to the base 24a of the archwire slot 24 does not pass through the center 22b of the base 22a of the body 22. Therefore, as shown in FIG. 8, it is not easy to coincide the base point 98 of the bracket 90 to the FA point 94 of the tooth 96.

However, with the bracket 21 of the present invention, as shown in FIGS. 1 and 2, in addition to the first slit 25, the second slits 26 (26A, 26B) as markers are formed along an outline that is generated by crossing a plane including the longitudinally extending center line 24b, on the base 24a of the archwire slot 24, of the archwire slot 24 and vertical to the base 24a of the archwire slot 24, and an outer surface of the body 22 and side surfaces of the tiewings 23 with each other, so that, as shown in FIG. 2, an end portion (base point) 26a of the slit 26 situated at an edge portion of the body 22 can be coincided to the mid-transverse plane 38 of the tooth 39, resulting in effective orthodontic treatment.

Next, the second embodiment of the present invention, in which a so-called torque-in-base-type bracket is used, will be explained with reference to FIGS. 3A to 3C and FIG. 4.

The torque-in-base-type bracket is, as shown in FIGS. 3C and 4, characterized in that the bracket 41 is provided with tiewings 43 (43A, 43B); bases 44a of slots 44 (44A, 44B) and a base 42a of a body 42 are not parallel with each other; and a plane including a longitudinally extending center line 44b, on the base 44a of the archwire slot 44, of the archwire slot 44 and vertical to the base 44a of the archwire slot 44 passes through the center 42b of the base 42a of the body 42.

With this bracket 41 of the present invention, in addition to the first slit 45 like the first slit 25 in the above first embodiment, the second slits 46 (46A, 46B) as markers are formed along an outline that is generated by crossing a plane including the longitudinally extending center line 44b, on the base 44a of the archwire slot 44, of the archwire slot 44 and vertical to the base 44a of the archwire slot 44, and an outer surface of the body 42 and side surfaces of the tiewings 43 with each other, so that, as shown in FIG. 4, an end portion (base point) 46a of the slit 46 situated at an edge portion of the body 42 can be coincided to the mid-transverse plane 58 of the tooth 59, resulting in effective orthodontic treatment.

The slits 25, 26, 45 and 46 as markers should not be formed on the overall outlines, but those may be placed near the edge portions (base points) 26a, 46a only. Further, the markers are not limited to slits, but protrusions, projections and notches may be used. Besides the slits 25, 26, 45 and 46 as markers, which are obtained by directly machining brackets, markers painted on the outer surface of brackets, which are utilized to position the brackets and are rubbed out after the positioning, may be included in the scope of this invention.

In addition, not only markers for positioning directly applied to brackets as described above, but also a jig mounted to a slot of a bracket and functioning, with a part of the jig, in the same manner as the slit or the like on at least a portion of the outline may be included in the scope of the present invention.

Next, the third embodiment of the present invention, which is especially suitable for the indirect boding method, will be explained. In this method, a bracket is preliminarily bonded on a model of the patient's row of teeth at a position where the bracket should be mounted, and then, the bracket is properly transported in the oral cavity of the patient and bonded to the patient's tooth.

As illustrated in FIGS. 5A to 5C, the bracket 61 is constructed such that an insert hole 62 is drilled from an outer surface of the bracket 61 to a portion just before a base 22a of the body 22 along a line passing through a point (target point) 27 that is generated by crossing a line, which is generated by crossing a plane including a longitudinally extending center line 24b, on the archwire slot base 24a of the archwire slot 24 and vertical to the archwire slot base 24a, and the body base 22a, and a plane vertical to the center line 24b of the archwire slot 24 and dividing the body 22 exactly into two parts. The insert hole 62 may be a through hole. When the hole 62 is a through hole and the bracket 61 is bonded to a patient's tooth through bonding agent, sometimes the bonding agent overflows from the hole, which may cause a wire not to be fastened to the archwire slot 24. Without such risk, the hole 62 is preferably a through hole.

To use this bracket 61, as shown in FIG. 6, a needle-like jig 71 is inserted into the insert hole 62 of the bracket 61, and the tip of the jig 71 is fixed to a portion just before an FA point 73, which is marked in advance on a tooth 74 on a model of a row of teeth to position the target point 27 on the base 22a of the body 22, and then, as described above, the second slits 26 of the bracket 61 and the mid-transverse plane 38 of the tooth 74 are coincided with each other to position the bracket 61 to the tooth 74. After that, with the transfer tray, registered in Japanese Utility Model No. 3097069 by the present applicant, or the like, the bracket 61 is accurately positioned on the patient's tooth with ease.

Although, in the third embodiment described above, the insert hole 62 is drilled on the body 22 of the torque-in-face-type bracket 21, the insert hole 62 may be applied to the torque-in-base-type bracket 41 shown in FIGS. 3A to 3C. Further, in the above-mentioned embodiments, after the insert hole 62 is positioned with the jig 71, the second slits 26 and the mid-transverse plane 38 are coincided with each other to properly position the bracket 61 to the outer surface of the tooth 74. Without the second slits 26, the bracket 61 can properly be positioned on the outer surface of the tooth by coinciding the center of the bracket and the FACC with each other in the same manner as a conventional method.

The above-mentioned brackets according to the present invention are applicable to all kinds of teeth including true molar teeth, and the present invention is applicable to brackets mounted on the tongue side also.

What is claimed is:

1. An orthodontic bracket having a body defining a body base and an archwire slot defining an archwire slot base, the body base and the archwire slot base being disposed in a non-parallel relationship with one another, the bracket being characterized by having a marker for indicating a direction of a face vertical to the bottom of said archwire slot, the marker being disposed within a plane orthogonal to the slot base, the marker extending along a longitudinally extending center line of said archwire slot, the marker extending along the body from the archwire slot base to the body base.

2. The orthodontic bracket as claimed in claim 1, wherein the marker is selected from the group consisting of a protrusion, a projection, a slit, a notch and a paint.

3. The orthodontic bracket of claim 2 wherein an insert hole is drilled from an outer surface of said bracket to a portion just before said body base along a line passing through a point that is generated by crossing a line, which is generated by crossing a plane including a longitudinally extending center line, on the archwire slot base of said archwire slot and vertical to the archwire slot base, and the body base, and a plane vertical to the center line of the archwire slot and dividing the body exactly into two parts.

4. The orthodontic bracket of claim 2 wherein a through hole penetrates the body from the body base to an outer surface of said bracket along a line passing through a point that is generated by crossing a line, which is generated by crossing a plane including a longitudinally extending center line, on the archwire slot base of said archwire slot and vertical to the archwire slot base, and the body base, and a plane vertical to the center line of the archwire slot and dividing the body exactly into two parts.

5. The orthodontic bracket of claim 1 wherein an insert hole is drilled from an outer surface of said bracket to a portion just before said body base along a line passing through a point that is generated by crossing a line, which is generated by crossing a plane including a longitudinally extending center line, on the archwire slot base of said archwire slot and vertical to the archwire slot base, and the body base, and a plane vertical to the center line of the archwire slot and dividing the body exactly into two parts.

6. The orthodontic bracket as claimed in claim 5, wherein said marker is selected from the group consisting of a protrusion, a projection, a slit, a notch and a paint.

7. The orthodontic bracket of claim 1 wherein a through hole penetrates the body from the body base to an outer surface of said bracket along a line passing through a point that is generated by crossing a line, which is generated by crossing a plane including a longitudinally extending center line, on the archwire slot base of said archwire slot and vertical to the archwire slot base, and the body base, and a plane vertical to the center line of the archwire slot and dividing the body exactly into two parts.

8. The orthodontic bracket as claimed in claim 7, wherein said marker is selected from the group consisting of a protrusion, a projection, a slit, a notch and a paint.

9. The orthodontic bracket as recited in claim 1, wherein the marker is removable from the body.

10. The orthodontic bracket as recited in claim 9, wherein the marker is erasable from the body.

11. The orthodontic bracket as recited in claim 1, wherein the bracket body defines a top surface, the body base being disposed in non-parallel relationship relative to the top surface.

12. An orthodontic bracket comprising a body having an outer surface, the body having a body base and an archwire slot including an archwire slot base defining a longitudinal slot base centerline, the body base and the archwire slot base being disposed in a non-parallel relationship with one another, the bracket being characterized by having a marker disposed on the outer surface, the marker being disposed in a plane including the longitudinal slot base centerline, the plane being perpendicular to the archwire slot base, the marker extending along the body from the body base to the archwire slot base.

13. The orthodontic bracket as claimed in claim 12, wherein said marker is selected from the group consisting of a protrusion, a projection, a slit, a notch and a paint.

14. The orthodontic bracket of claim 13 wherein an insert hole is drilled from the outer surface to a portion just before said body base along a line passing through a point that is generated by crossing a line, which is generated by crossing a plane including a longitudinally extending center line, on the archwire slot base of said archwire slot and vertical to the archwire slot base, and the body base, and a plane vertical to the center line of the archwire slot and dividing the body exactly into two parts.

15. The orthodontic bracket of claim 13 wherein a through hole penetrates the body from the body base to the outer surface along a line passing through a point that is generated by crossing a line, which is generated by crossing a plane including a longitudinally extending center line, on the archwire slot base of said archwire slot and vertical to the archwire slot base, and the body base, and a plane vertical to the center line of the archwire slot and dividing the body exactly into two parts.

16. The orthodontic bracket of claim 12 wherein an insert hole is drilled from the outer surface to a portion just before said body base along a line passing through a point that is generated by crossing a line, which is generated by crossing a plane including a longitudinally extending center line, on the archwire slot base of said archwire slot and vertical to the archwire slot base, and the body base, and a plane vertical to the center line of the archwire slot and dividing the body exactly into two parts.

17. The orthodontic bracket of claim 12 wherein a through hole penetrates the body from the body base to the outer surface along a line passing through a point that is generated by crossing a line, which is generated by crossing a plane including a longitudinally extending center line, on the archwire slot base of said archwire slot and vertical to the archwire slot base, and the body base, and a plane vertical to the center line of the archwire slot and dividing the body exactly into two parts.

18. The orthodontic bracket as recited in claim 12, wherein the marker is removable from the body.

19. The orthodontic bracket as recited in claim 12, wherein the bracket body defines a top surface, the body base being disposed in non-parallel relationship relative to the top surface.

20. An orthodontic bracket having a body defining a body base and an archwire slot defining an archwire slot base, the body base and the archwire slot base being disposed in a non-parallel relationship with one another, the bracket being characterized by having a marker disposed within a plane orthogonal to the slot base, the marker extending along a longitudinally extending center line of said archwire slot, with the marker extending along the body from the body base toward the archwire slot base.

* * * * *